US00PP22100P2

(12) United States Plant Patent
Madsen

(10) Patent No.: US PP22,100 P2
(45) Date of Patent: Aug. 30, 2011

(54) ***SCHLUMBERGERA* PLANT NAMED 'PKMSC02'**

(50) Latin Name: *Schlumbergera truncata*
Varietal Denomination: PKMSC02

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 12/660,788

(22) Filed: Mar. 4, 2010

(51) Int. Cl.
*A01H 5/00* (2006.01)

(52) U.S. Cl. ..... Plt./372

(58) Field of Classification Search ..... Plt./263.1, Plt./372
See application file for complete search history.

*Primary Examiner* — Susan McCormick Ewoldt
(74) *Attorney, Agent, or Firm* — Foley & Lardner LLP

(57) ABSTRACT

A new and distinct *Schlumbergera truncata* plant named 'PKMSC02' particularly characterized by large upright to vertical flowers; flowers which have petals which are greyed-orange (RHS 169A) and a red-purple throat (RHS 71D); large quantity of flowers per plant; moderately vigorous and freely branching habit; and ovoid to lanceolatoid buds, which are greyed-orange (RHS 169A) in color.

11 Drawing Sheets

Latin name of the genus and species of the plant claimed: *Schlumbergera truncata.*

Variety denomination: 'PKMSC02'.

BACKGROUND OF THE INVENTION

The present invention relates to a new and distinct cultivar of *Schlumbergera* plant, botanically known as *Schlumbergera truncate* (Haworth) Moran., commonly known as Christmas Cactus, and hereinafter referred to by the cultivar name 'PKMSC02'.

*Schlumbergera* (formerly *Zygocacatus*) of the Cactaceae family, consists of 6 known species which are epiphytic cacti and native to Brazil. Common names for *Schlumbergera* plants include: Crab Cactus for the cultivar's claw-like phylloclade margin, Thanksgiving Cactus for cultivars which bloom in November, and Christmas Cactus for cultivars which bloom in December.

The new *Schlumbergera* 'PKMSC02' is a product of a controlled breeding program conducted by the inventor, Christian Hald Madsen, in Søhus, Denmark. The objective of the breeding program was to develop a new *Schlumbergera* cultivar with an upright and compact plant habit and flowers with a unique color combination. The new *Schlumbergera* 'PKMSC02' originated from a cross made by the inventor, Christian Hald Madsen, in 2002 in Søhus, Denmark, between two unnamed, unpatented proprietary *Schlumbergera truncate* (Haworth) Moran. cultivars. The new *Schlumbergera* 'PKMSC02' was discovered and selected by the inventor as a single flowering plant within the progeny of the stated cross in a controlled environment in 2004 in Søhus, Denmark. The inventor selected the new *Schlumbergera* 'PKMSC02' based on its compact, freely branching habit and unique flower color.

Asexual reproduction of the new *Schlumbergera* 'PKMSC02' by phylloclade cuttings, followed by trial production batches, was first performed in May of 2006 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'PKMSC02' which in combination distinguish this *Schlumbergera* as a new and distinct cultivar:

1. Large upright to vertical flowers;
2. Flowers which have petals which are greyed-orange (RHS 169A) and a red-purple throat (RHS 71D);
3. Large quantity of flowers per plant;
4. Moderately vigorous and freely branching habit; and
5. Ovoid to lanceolatoid buds, which are greyed-orange (RHS 169A) in color.

No plants of either parent, both an unnamed, unpatented proprietary *Schlumbergera truncate* (Haworth) Moran. line, are available to provide a botanical comparison to the new *Schlumbergera* 'PKMSC02'.

Of the many commercial cultivars known to the present inventor, the most similar in comparison to the new *Schlumbergera* 'PKMSC02' is the *Schlumbergera truncate* (Haworth) Moran. 'Beach Dancer'. In side-by-side comparisons trials conducted over several seasons by the inventor in Søhus, Denmark, plants of 'PKMSC02' differ from plants of 'Beach Dancer' in the following characteristics:

1. Plants of 'PKMSC02' are more compact in size (measuring about 10 cm to 11 cm in height and about 15 cm to 17 cm in spread) than plants of 'Beach Dancer' (measuring about 18 cm in height and about 24.5 cm in spread);
2. Plants of 'PKMSC02' produce shorter lateral branches (measuring about 7.5 cm) than plants of 'Beach Dancer' (lateral branches measuring about 15.5 cm);
3. Plants of 'PKMSC02' produce smaller phyllocladia (measuring about 3.5 cm in length, about 2.5 cm in width, and about 2 mm in thickness) than plants of 'Beach Dancer' (phyllocladia measuring about 4.5 cm in length, about 3.5 cm in width, and about 4 mm in thickness);

4. Plants of 'PKMSC02' produce buds and flowers with the same color (greyed-orange, RHS 169A), whereas plants of 'Beach Dancer' produce buds and flowers with different colors (orange, RHS 27A bud color, and red, RHS 37A flower color); and
5. Plants of 'PKMSC02' produce a striking flower color combination of greyed-orange (RHS 169A) petals with a red-purple (RHS 71D) throat, whereas plants of 'Beach Dancer' produce flowers with a color combination of red (RHS 37A) petals with a white (RHS NN155D) throat.

BRIEF DESCRIPTION OF THE PHOTOGRAPHS

The accompanying photographs illustrate the overall appearance of the new *Schlumbergera* cultivar 'PKMSC02' showing the colors as true as is reasonably possible with colored reproductions of this type. Colors in the photographs may differ slightly from the color values cited in the detailed botanical description, which accurately describe the color of 'PKMSC02'.

DETAILED BOTANICAL DESCRIPTION

Figure 1:
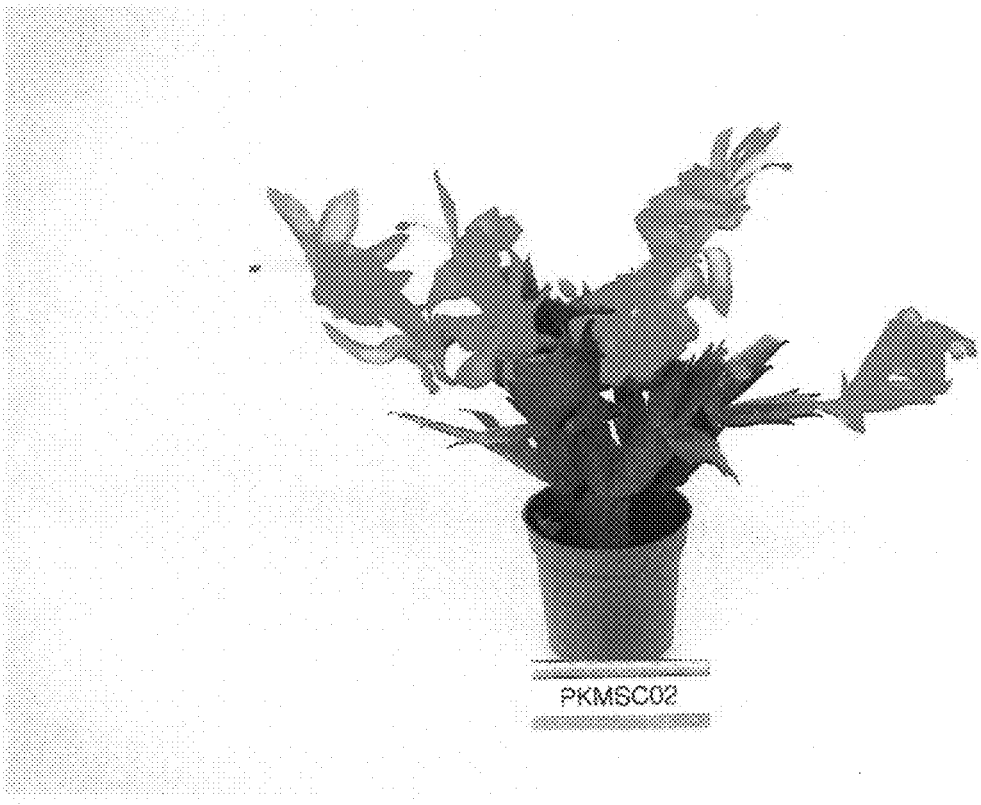
FIG. 1 shows a side perspective view of a typical flowering plant of 'PKMSC02', grown in a 5.5. cm pot, at about 7 months of age.
Figure 2:
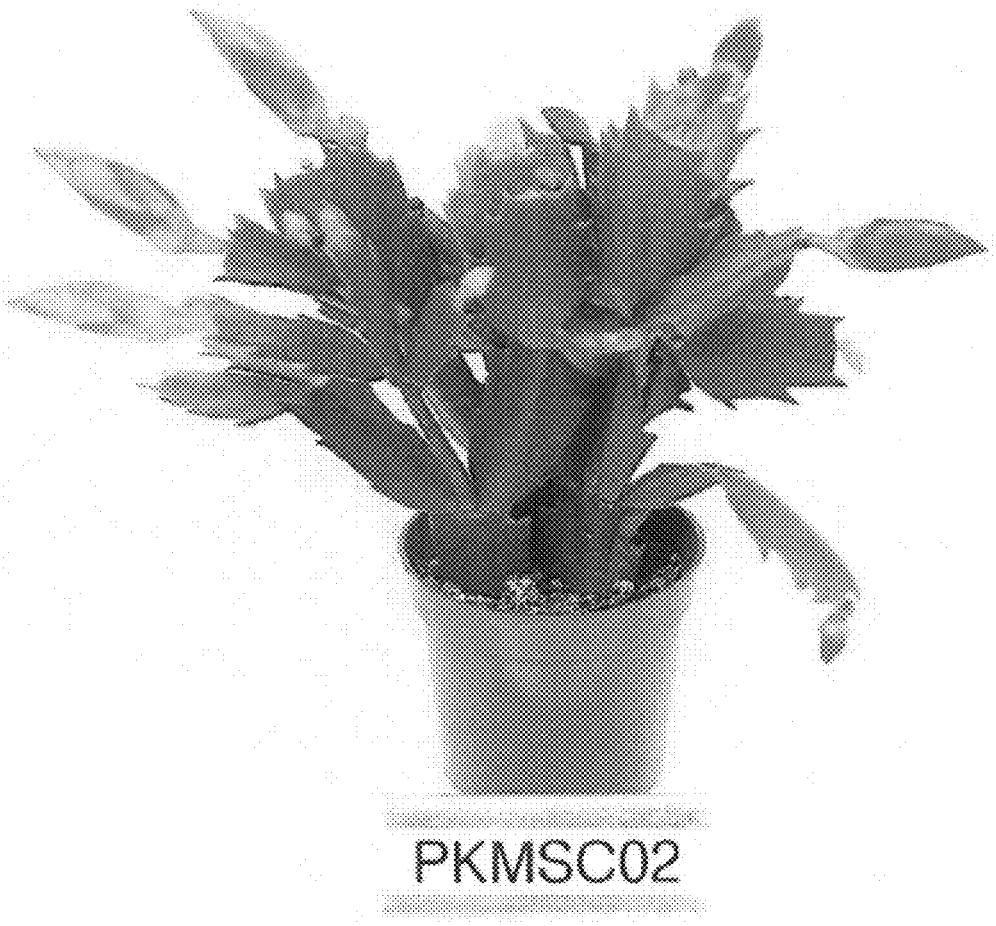
FIG. 2 shows a side perspective view of a typical plant of 'PKMSC02' with buds, grown in a 5.5 cm pot, at about 6 months of age.
Figure 3:
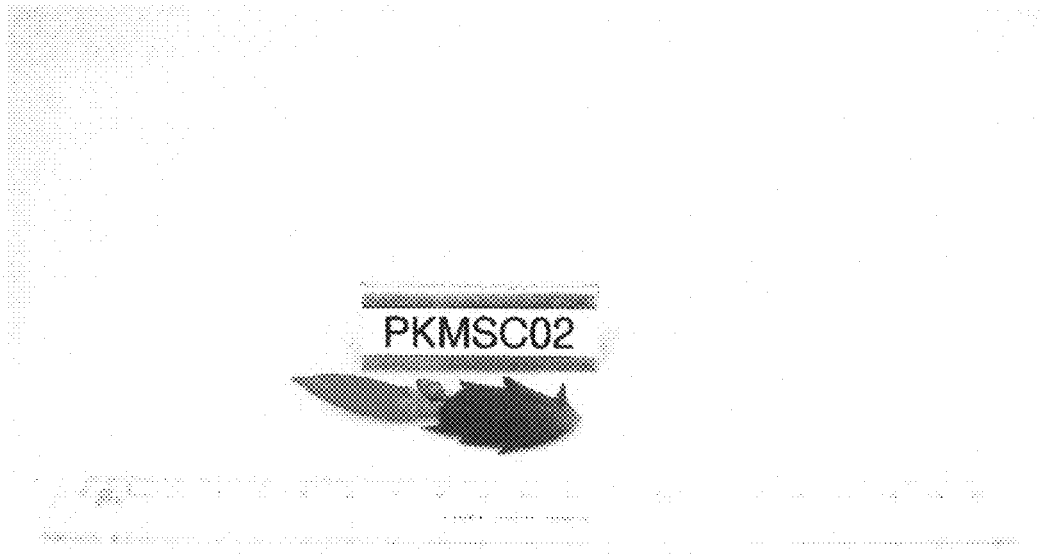
FIG. 3 shows a close-up view of a typical mature bud of 'PKMSC02'.
Figure 4:
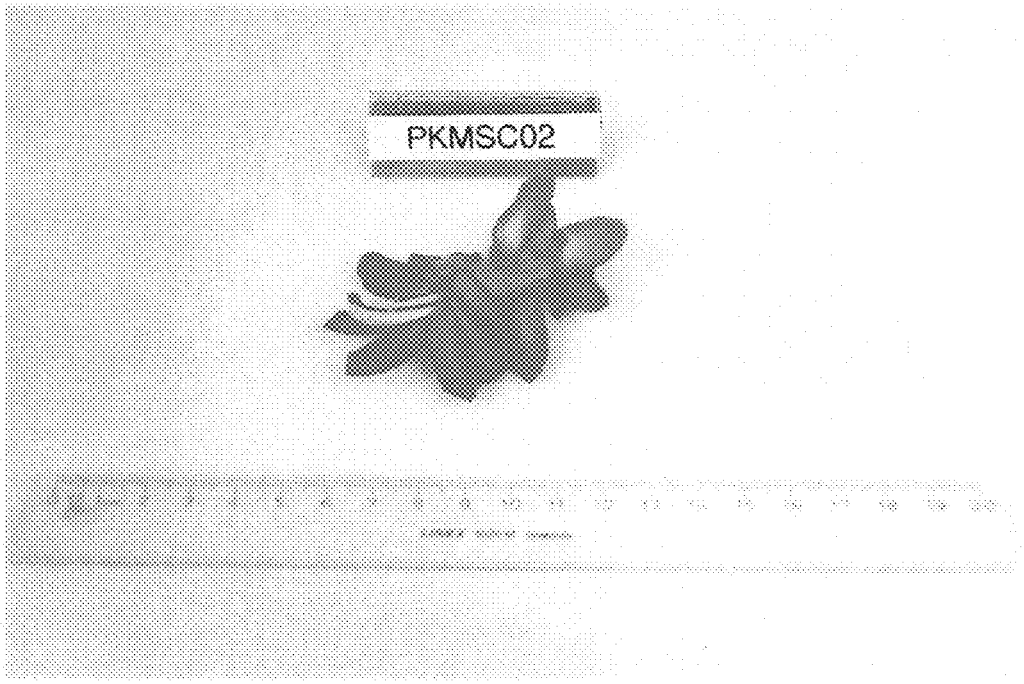
FIG. 4 shows a close-up view of a typical fully-opened flower of 'PKMSC02'.
Figure 5:
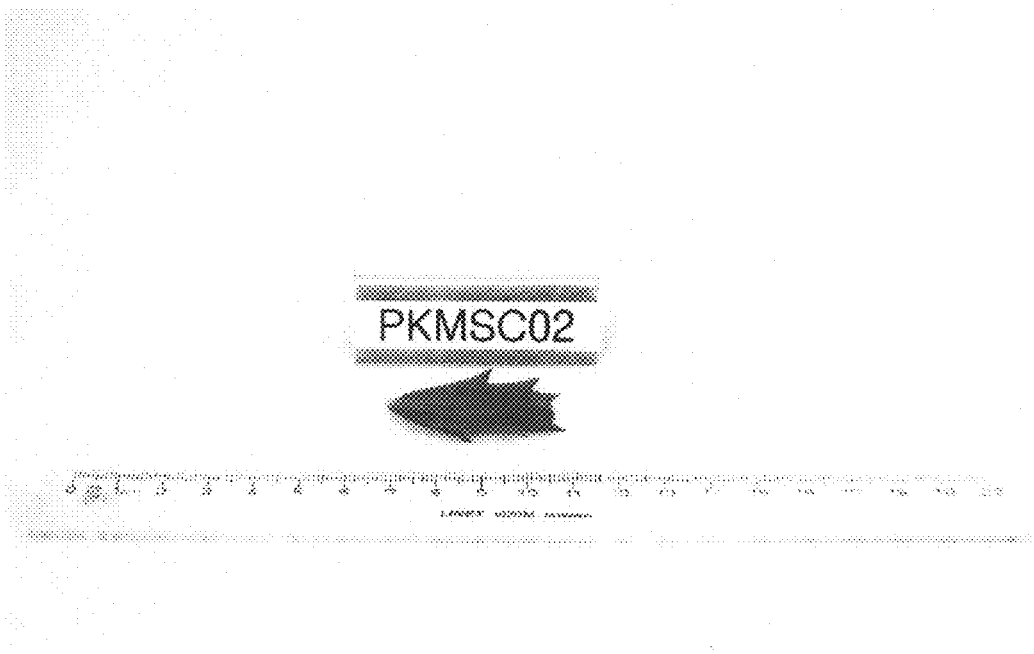
FIG. 5 shows a close-up view of a typical mature phylloclade of 'PKMSC02'.
Figure 6:
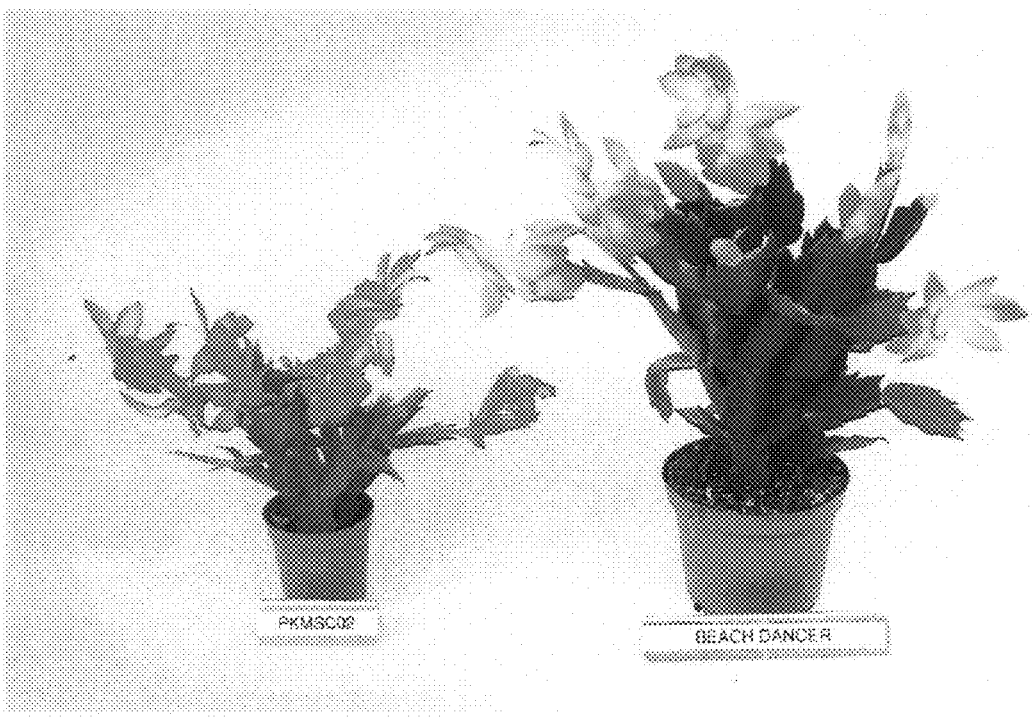
FIG. 6 shows a side comparison view of a typical flowering plant of 'PKMSC02' (on the left) and a typical flowering plant of the comparison cultivar 'Beach Dancer' (on the right).
Figure 7:
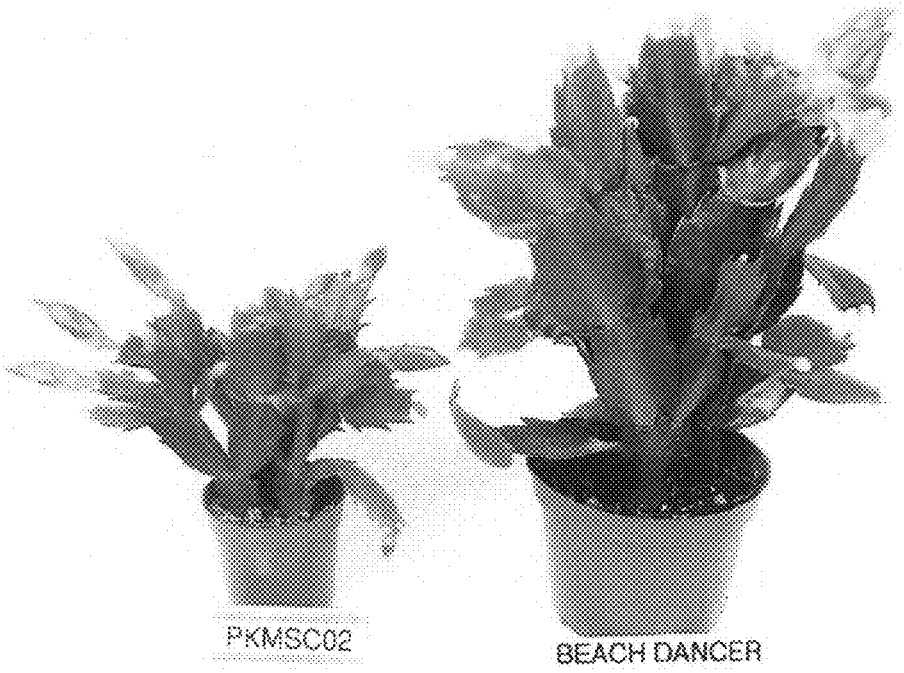
FIG. 7 shows a side comparison view of a typical plant of 'PKMSC02' with buds (on the left) and a typical plant of the comparison cultivar 'Beach Dancer' with buds (on the right).
Figure 8:
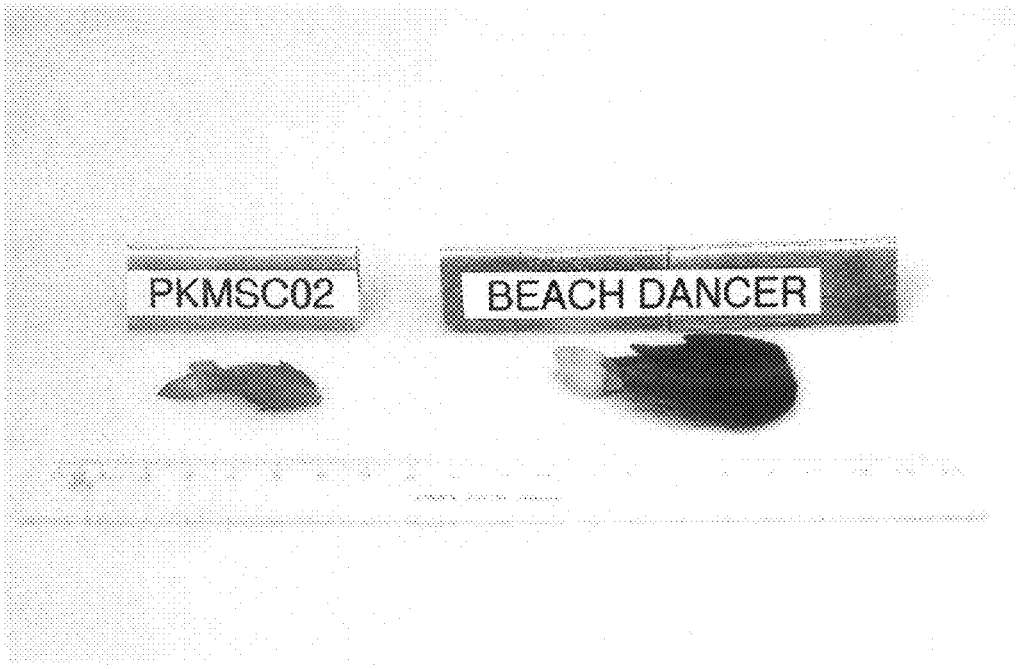
FIG. 8 shows a close-up comparison view of a typical young bud and phylloclade of 'PKMSC02' (on the left) and a typical young bud and phylloclade of the comparison cultivar 'Beach Dancer' (on the right).
Figure 9:
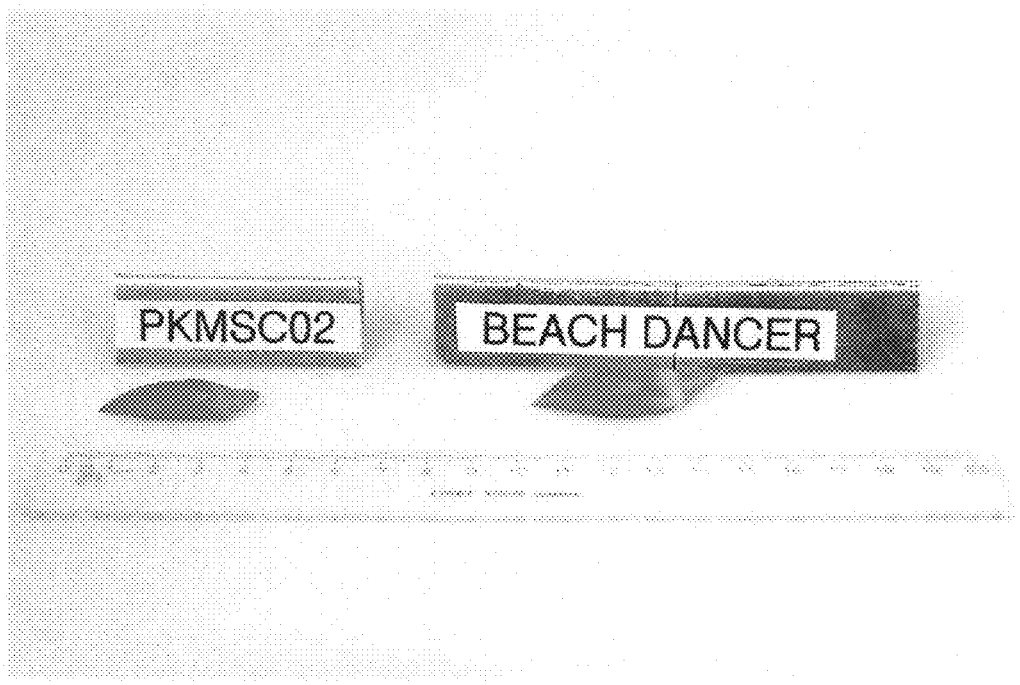
FIG. 9 shows a close-up comparison view of a typical mature bud of 'PKMSC02' (on the left) and a typical mature bud of the comparison cultivar 'Beach Dancer' (on the right).
Figure 10:
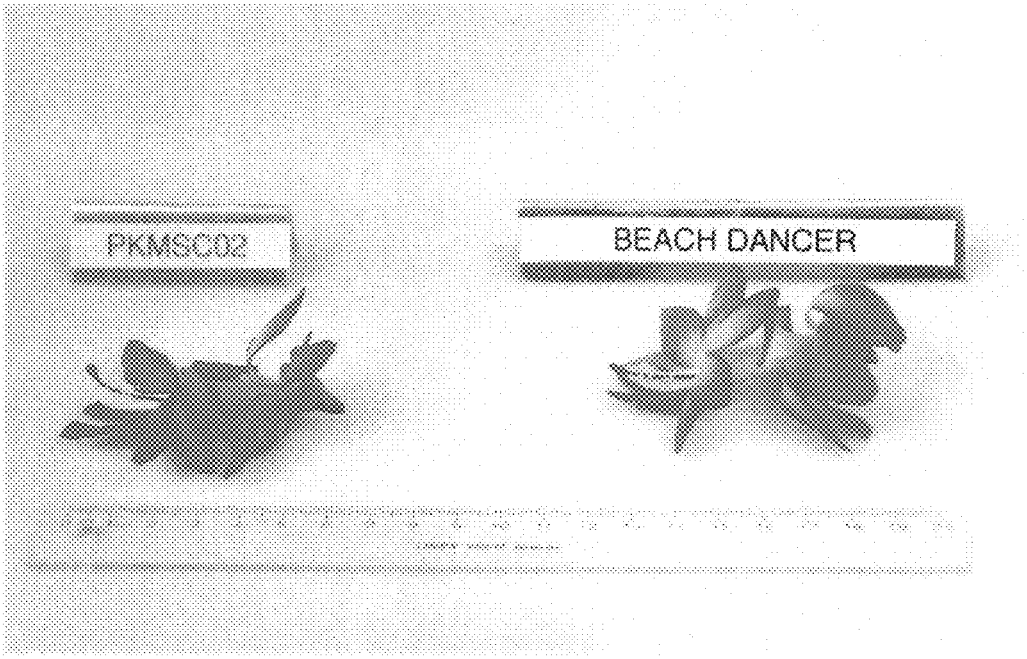
FIG. 10 shows a close-up comparison view of a typical fully-opened flower of 'PKMSC02' (on the left) and a typical fully-opened flower of the comparison cultivar 'Beach Dancer' (on the right).
Figure 11:
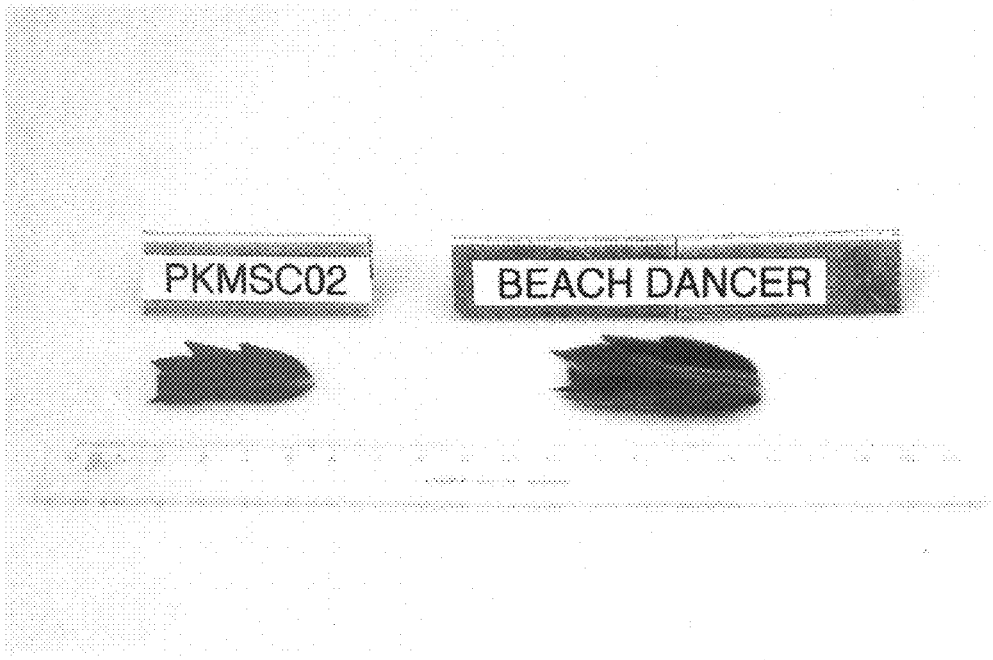
FIG. 11 shows a close-up comparison view of a typical mature phylloclade of 'PKMSC02' (on the left) and a typical mature phylloclade of the comparison cultivar 'Beach Dancer' (on the right).

The new *Schlumbergera* 'PKMSC02' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PKMSC02' as grown in a glass-covered greenhouse in Fyn, Denmark, under conditions which closely approximate those generally used in commercial practice. Plants of 'PKMSC02' are thermo-photo-periodic and will develop buds and bloom best under short day conditions (less than 12 hours of sunlight for a period of 6 weeks) and cool night temperatures between 15° C. and 18° C. Plants of 'PKMSC02' are grown under an average day temperate of 18° C. and an average night temperature of 18° C. Ambient light levels of +120W m2 were used and no growth retardants were applied when growing plants of 'PKMMSC02'.

Color references are made to The Royal Horticultural Society Colour Chart (R.H.S.), $4^{th}$ edition, except where general colors of ordinary significance are used. The photographs and descriptions were taken during the winter season of 2009 in Fyn, Denmark, when outdoor day temperatures averaged 5° C. and outdoor night temperatures averaged 0° C. The age of the plants described is about 24 weeks after rooting of cutting.

Classification:

*Botanical.*—*Schlumbergera truncata.*

*Common name.*—Christmas Cactus.

Parentage:

*Female or seed parent.*—Unnamed, unpatented proprietary *Schlumbergera truncate* (Haworth) Moran. cultivar.

*Male or pollen parent.*—Unnamed, unpatented proprietary *Schlumbergera truncate* (Haworth) Moran. cultivar.

Propagation: By single, mature phylloclade cuttings.

*Time and temperature to initiate roots.*—In a greenhouse, about 16 days at 21° C.

*Time and temperature to produce a rooted cutting.*—In a greenhouse, about 35 days at at 21° C.

*Rooting habit and description.*—Fine, fibrous and well-branched.

Plant:

*Type.*—Perennial, Epiphyte.

*Growth habit.*—Young plants have erect and upright habit. Mature plants become slightly pendent as lateral branches lengthen.

*Branching habit.*—Freely branching, with two or three phylloclades forming at the apical ends of older phylloclades. Single or double (seldomly triple) sessile flowers borne on apical end of phylloclades.

*Vigor.*—Moderately vigorous.

*Crop time.*—After rooting of mature phylloclade cutting, about 12 months are required to produce a finished flowering plant in an 5.5 cm pot.

*Size at maturity.*—Height (soil level to top of plant, including flowers): About 10 cm to 11 cm. Spread: About 15 cm to 17 cm.

Stem: None, older phylloclades may turn woody with age (several years).

Lateral branches:

*Arrangement.*—Phylloclades form at the apical end of older phylloclades to form branches.

*Branching habit.*—Freely.

*Basal branching.*—Yes.

*Quantity.*—About 9 to 12.

*Length.*—Primary: About 3.5 cm (1 phylloclade). Secondary: About 7 cm to 8 cm (2 or 3 phylloclades).

*Width.*—About 2 cm to 3 cm.

*Aspect.*—Upright (from basal phylloclade).

*Strength.*—Strong (from basal phylloclade).
*Appearance.*—Glabrous, smooth.
*Pubescence.*—None.
*Color.*—Green, RHS 137A.

Phylloclade:
*Arrangement.*—Single and sequential.
*Quantity per lateral branch.*—About 3 to 4.
*Length.*—About 3 cm to 4 cm.
*Width.*—About 2 cm to 3 cm.
*Thickness.*—About 2 mm (center of phylloclade).
*Overall shape.*—Oval.
*Apex shape.*—Truncate with 2 protruding marginal teeth (about 5 mm in length), forming a claw-like shape.
*Base shape.*—Rounded.
*Margin.*—Serrated; about 2 to 4 teeth (about 5 mm in length).
*Texture.*—Glabrous, smooth.
*Pubescence.*—None.
*Color of upper surface.*—Immature: Green, RHS 137A; Mature: Green, RHS 137A; Margin: Green, RHS 137A.
*Color of lower surface.*—Immature: Green, RHS 137A; Mature: Green, RHS 137A; Margin: Green, RHS 137A.
*Venation.*—Pattern: Costate. Color: Upper surface: Green, RHS 137C; Lower surface: Green, RHS 137C.

Areole: Not true areole structure; tip of phylloclade is barbellulate with about 10 to 15 stiff hairs, but no true areole structures.

Inflorescence description:
*Arrangement and appearance.*—Single or double (seldom triple) sessile flowers borne on apical end of phylloclades. Flowers are hose-in-hose and zygomorphic. When flowers are fully open, they form a right angle to the phylloclade. Flowers persistent; petals fold and wither slowly.
*Natural flowering season.*—Flowering occurs from October to January (Northern hemisphere), but can be changed depending on short day photo-treatments.
*Flowering response time.*—About 8 to 9 weeks from planting.
*Rate of flowers opening.*—About 1 to 2 per week, depending on temperature and light.
*Flowering longevity* (*dependent on temperature and light conditions*).—About 5 to 6 days.
*Fragrance.*—None.
*Quantity of flowers per lateral branch.*—About 1 to 3.
*Quantity of buds per lateral branch.*—About 2.
*Quantity of flowers and buds per plant.*—About 25 to 30.
*Flower bud.*—Length: Ranging from 0 to 3.5 cm (before anthesis). Width: Ranging up to 1 cm (before anthesis). Shape: Ovoid to lanceolate. Color: Greyed-orange, RHS 169A.
*Flower.*—Type: Single. Shape: Tubular, hose-in-hose triple perianth. Aspect: Initially upright, later facing outward (right angle to phylloclade). Persistent or self-cleaning: Persistent, but drops after withering.
*Corolla size.*—Depth: About 7 cm (including ovary). Diameter: About 5 cm to 6 cm. Tube length: About 30 mm. Tube diameter: About 8 mm.
*Petals.*—Quantity: Apical Whorl: About 5 to 7; Basal whorl: About 10. Length: About 1.2 cm to 3.8 cm. Width: About 1.0 cm to 1.4 cm. Overall shape: Oval. Apex shape: Retuse. Base shape: Apical Whorl: Fused; Basal Whorl: Free. Margin: Entire. Appearance: Smooth. Texture: Silky (both surfaces). Color of Upper Surface (when opening and when fully opened): Lobe: Greyed-orange, RHS 169A; Tube: Red-purple, RHS 71D. Color of Under Surface (when opening and when fully opened): Lobe: Greyed-orange, RHS 169A; Tube: Red-purple, RHS 71D. Color Fades to: Greyed-orange, RHS 172A.
*Petaloids.*—None.
*Calyx.*—Shape: Tube. Length: Up to 1 mm. Diameter: Up to 5 mm.
*Sepals.*—Appearance: Same as petals. Arrangement: Free. Quantity: About 4. Length: Up to 8 mm. Width: Up to 6 mm. Overall shape: Ovate. Apex shape: Obtuse to rounded. Base shape: Truncate. Margin: Entire. Texture (both surfaces): Silky. Color (Immature and Mature): Upper and Under Surfaces: Greyed-orange, RHS 169A.

Reproductive organs:
*Androecium.*—Stamen: Quantity: Many (about 70 to 80), polyandrous, incurved. Some filaments fused to perianth tube (connate); about 5 mm from receptacle. Length: About 50 mm. Color: Translucent, white, RHS 155D. Anther: Shape: Basifixed, ovoid. Length: About 1 mm. Color: Yellow, RHS 11C. Filament: Length: About 40 mm to 45 mm. Color: Translucent, white, RHS 155D. Pollen: Amount: Abundant. Color: Yellow, RHS 11D.
*Gynoecium.*—Pistil: Quantity: 1. Shape: Slightly curved. Length: About 55 mm. Stigma: Shape: Claw-like. Color: Red-purple, RHS 71A. Style: Length: About 50 mm. Color: Red-purple, RHS 71A. Ovary: Shape: Angular. Length: About 4 mm to 5 mm. Width: About 3 mm. Color: Yellow-green, RHS 144A.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about +2° C. and to a high temperature about +40° C.

Drought tolerance: Good.

What is claimed is:

1. A new and distinct *Schlumbergera truncata* plant named 'PKMSC02', as illustrated and described herein.

* * * * *